United States Patent
Giffard et al.

(10) Patent No.: US 9,889,415 B2
(45) Date of Patent: Feb. 13, 2018

(54) VACUUM INDICATOR SYSTEM THAT AVOID RELEASE WITHOUT THE PROPER VACUUM LEVEL

(71) Applicant: Biomet SAS, Valence (FR)

(72) Inventors: Lenaic Giffard, Valence (FR); Cedric Cauquot, Valence (FR); Alexis Dupuy, Valence (FR)

(73) Assignee: Biomet SAS, Valence (FR)

( * ) Notice: Subject to any disclaimer, the term of this patent is extended or adjusted under 35 U.S.C. 154(b) by 0 days.

(21) Appl. No.: 15/670,476

(22) Filed: Aug. 7, 2017

(65) Prior Publication Data
US 2017/0341042 A1  Nov. 30, 2017

Related U.S. Application Data

(63) Continuation of application No. 15/371,592, filed on Dec. 7, 2016, now Pat. No. 9,724,661, which is a
(Continued)

(51) Int. Cl.
*A61B 17/88* (2006.01)
*B01F 13/06* (2006.01)
(Continued)

(52) U.S. Cl.
CPC .......... *B01F 13/06* (2013.01); *A61B 17/8802* (2013.01); *A61B 17/8825* (2013.01);
(Continued)

(58) Field of Classification Search
CPC ............ A61B 17/8833; A61B 17/8802; A61B 17/8825; A61B 2017/8838; B01F 11/0054;
(Continued)

(56) References Cited

U.S. PATENT DOCUMENTS 4,019,629 A    4/1977  Dubner et al.
4,178,932 A   12/1979  Ryder et al.
(Continued)

FOREIGN PATENT DOCUMENTS

EP    1020167 A2   7/2000
EP    1741413 A1   1/2007
(Continued)

OTHER PUBLICATIONS

"U.S. Appl. No. 14/050,983, Notice of Allowance dated Sep. 12, 2016", 10 pgs.
(Continued)

*Primary Examiner* — Charles Cooley
*Assistant Examiner* — Marc C Howell
(74) *Attorney, Agent, or Firm* — Schwegman Lundberg & Woessner, P.A.

(57) ABSTRACT

A device for storing and mixing bone cement components. The device includes a housing, a safety device, and a vacuum indicator. The housing defines a mixing chamber configured to store a first bone cement component therein. In a first safety position, the safety device prevents contact between the first bone cement component and a second bone cement component in the mixing chamber. In a second safety position, the safety device permits contact between the first and second bone cement components in the mixing chamber. The vacuum indicator restricts movement of the safety device from the first safety position to the second safety position when in a first vacuum indicator position. The vacuum indicator permits movement of the safety device from the first safety position to the second safety position when in a second vacuum indicator position.

20 Claims, 9 Drawing Sheets

Related U.S. Application Data continuation of application No. 14/050,983, filed on Oct. 10, 2013, now Pat. No. 9,549,770.

(51) Int. Cl.

| | | |
|---|---|---|
| *B01F 15/00* | (2006.01) | |
| *B01F 11/00* | (2006.01) | |
| *B01F 15/02* | (2006.01) | |
| *B01F 13/04* | (2006.01) | |
| *B01F 13/00* | (2006.01) | |
| *A61B 17/00* | (2006.01) | |

(52) U.S. Cl.
CPC ...... *A61B 17/8827* (2013.01); *A61B 17/8833* (2013.01); *B01F 11/0054* (2013.01); *B01F 11/0082* (2013.01); *B01F 13/002* (2013.01); *B01F 13/0033* (2013.01); *B01F 13/047* (2013.01); *B01F 15/00331* (2013.01); *B01F 15/00506* (2013.01); *B01F 15/0206* (2013.01); *B01F 15/0226* (2013.01); *B01F 15/0258* (2013.01); *A61B 2017/00115* (2013.01); *A61B 2017/8838* (2013.01); *B01F 2215/0029* (2013.01)

(58) Field of Classification Search
CPC  B01F 11/0082; B01F 13/002; B01F 13/0033; B01F 13/045; B01F 13/047; B01F 15/00331; B01F 15/00506; B01F 15/0206; B01F 15/0226; B01F 15/0258
USPC .............................. 366/76.93, 139
See application file for complete search history.

(56) References Cited

U.S. PATENT DOCUMENTS

| | | |
|---|---|---|
| 4,222,276 A | 9/1980 | Derogatis |
| 5,348,391 A | 9/1994 | Murray |
| 5,368,386 A | 11/1994 | Murray |
| 5,395,167 A | 3/1995 | Murray |
| 5,549,381 A | 8/1996 | Hays et al. |
| 5,586,821 A | 12/1996 | Bonitati et al. |
| 5,624,184 A | 4/1997 | Chan |
| 5,788,463 A | 8/1998 | Chan |
| 5,797,680 A | 8/1998 | Murray |
| 5,803,282 A | 9/1998 | Chen et al. |
| 5,934,803 A | 8/1999 | Hutter |
| 6,042,262 A | 3/2000 | Hajianpour |
| 6,120,174 A | 9/2000 | Hoag et al. |
| 6,176,607 B1 | 1/2001 | Hajianpour |
| 6,210,031 B1 | 4/2001 | Murray |
| 9,549,770 B2 | 1/2017 | Giffard |
| 9,724,661 B2 | 8/2017 | Giffard et al. |
| 2007/0016215 A1 | 1/2007 | Wilander et al. |
| 2010/0046315 A1 | 2/2010 | Merkhan et al. |
| 2012/0071884 A1 | 3/2012 | Cooper et al. |
| 2015/0103616 A1 | 4/2015 | Giffard et al. |
| 2016/0051304 A1 | 2/2016 | Vogt et al. |
| 2016/0051305 A1 | 2/2016 | Vogt et al. |
| 2017/0080396 A1 | 3/2017 | Giffard et al. |

FOREIGN PATENT DOCUMENTS

| | | |
|---|---|---|
| EP | 2578308 A2 | 4/2013 |
| WO | WO-9906140 A1 | 2/1999 |
| WO | WO-2015052692 A1 | 4/2015 |

OTHER PUBLICATIONS

"U.S. Appl. No. 14/050,983, Response filed Jun. 7, 2016 to Restriction Requirement dated Apr. 7, 2016", 8 pgs.

"U.S. Appl. No. 14/050,983, Restriction Requirement dated Apr. 7, 2016", 7 pgs.

"U.S. Appl. No. 15/371,592, Final Office Action dated Mar. 30, 2017", 10 pgs.

"U.S. Appl. No. 15/371,592, Non Final Office Action dated Jan. 9, 2017", 5 pgs.

"U.S. Appl. No. 15/371,592, Notice of Allowance dated Jun. 15, 2017", 5 pgs.

"U.S. Appl. No. 15/371,592, Response filed Jan. 19, 2017 to Non Final Office Action dated Jan. 9, 2017", 8 pgs.

"U.S. Appl. No. 15/371,582, Response filed May 18, 2017 to Final Office Action dated Mar 30, 2017", 8 pgs.

"European Application Serial No. 14795869.8, Response filed Dec. 8, 2016 to Communication pursuant to Rules 161(1) and 162 EPC dated May 30, 2016", 11 pgs.

"International Application Serial No. PCT/IB2014/065224, International Preliminary Report on Patentability dated Apr. 21, 2016", 10 pgs.

"International Application Serial No. PCT/IB2014/065224, International Search Report dated Jan. 28, 2015", 5 pgs.

"International Application Serial No. PCT/IB2014/065224, Written Opinion dated Jan. 28, 2015", 8 pgs.

VACUUM INDICATOR SYSTEM THAT AVOID RELEASE WITHOUT THE PROPER VACUUM LEVEL

PRIORITY APPLICATIONS

This application is a continuation of U.S. patent application Ser. No. 15/371,592, filed Dec. 7, 2016, now U.S. Pat. No. 9,724,661 issued on Aug. 8, 2017, which application is a continuation of U.S. patent application Ser. No. 14/050,983, filed Oct. 10, 2013, now U.S. Pat. No. 9,549,770, filed Jan. 24, 2017.

FIELD

The present disclosure relates to a vacuum indicator for a bone cement storage and mixing device that restricts operation when predetermined vacuum level has not been reached.

BACKGROUND

This section provides background information related to the present disclosure, which is not necessarily prior art.

Bone cement can be used for artificial joint fixation and in a variety of surgical procedures to repair damaged bone, such as by filling bone defects. Bone cement is often made from a powder component and a liquid component, which are mixed just prior to or during the surgical procedure. To maintain the sterility of the bone cement and facilitate handling during the surgery, the liquid and powder components are stored and mixed within a single device. To enhance the quality of the bone cement, the liquid and powder components are mixed under a vacuum below a predetermined pressure, typically by surgical staff. To help surgical staff identify when the predetermined pressure has been reached, it would be advantageous for the device to have a visual indicator, as well as a feature to prevent mixture of the liquid and powder components unless the predetermined pressure has been reached.

SUMMARY

This section provides a general summary of the disclosure, and is not a comprehensive disclosure of its full scope or all of its features.

The present teachings provide for a device for storing and mixing bone cement components. The device includes a housing, a safety device, and a vacuum indicator. The housing defines a mixing chamber configured to store a first bone cement component therein. The safety device is movable between a first safety position and a second safety position. In the first safety position, the safety device prevents contact between the first bone cement component and a second bone cement component in the mixing chamber. In the second safety position, the safety device permits contact between the first and second bone cement components in the mixing chamber. The vacuum indicator is configured to move from a first vacuum indicator position to a second vacuum indicator position when pressure within the mixing chamber falls below a threshold value. The vacuum indicator restricts movement of the safety device from the first safety position to the second safety position when in the first vacuum indicator position. The vacuum indicator permits movement of the safety device from the first safety position to the second safety position when in the second vacuum indicator position.

The present teachings further provide for a device for storing and mixing bone cement components. The device includes a housing defining a mixing chamber configured to store a powder bone cement component therein. A first container support is slidably mounted to an exterior of the housing and movable from a first position to a second position in which the first container support is closer to the housing than in the first position. A first container configured to be mounted to the first container support. The first container is configured to store a liquid bone cement component therein. A first piercing cannula is in communication with the mixing chamber and extends from the housing. The first piercing cannula is proximate to the first container support. A safety insert is removably coupled to the housing and includes a first arm. The first arm is configured to extend between the first container support and the housing to restrict movement of the first container support from the first position to the second position. A vacuum indicator is movable from an extended position in which the vacuum indicator is configured to couple with the safety insert to restrict removal of the safety insert from cooperation with the housing, to a retracted position in which the vacuum indicator is not configured to couple with the safety insert in response to a reduction in pressure of the mixing chamber.

The present teachings also provide for a method for storing and mixing bone cement components. The method includes creating a vacuum within a mixing chamber containing a first bone cement component to decrease pressure therein below a threshold level, thereby causing a vacuum indicator to move from a first indicator position to a second indicator position, in the first indicator position the vacuum indicator restricts movement of a safety device from a first safety position to a second safety position, in the first safety position the safety device restricts contact between the first bone cement component and a second bone cement component in the mixing chamber, in the second position the vacuum indicator permits movement of the safety device to the second safety position in which the safety device does not obstruct contact between the first bone cement component and the second bone cement component in the mixing chamber; moving the safety device from the first safety position to the second safety position; mixing the first and second bone cement components together in the mixing chamber to form a bone cement mixture; and dispensing the bone cement mixture from within the mixing chamber.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
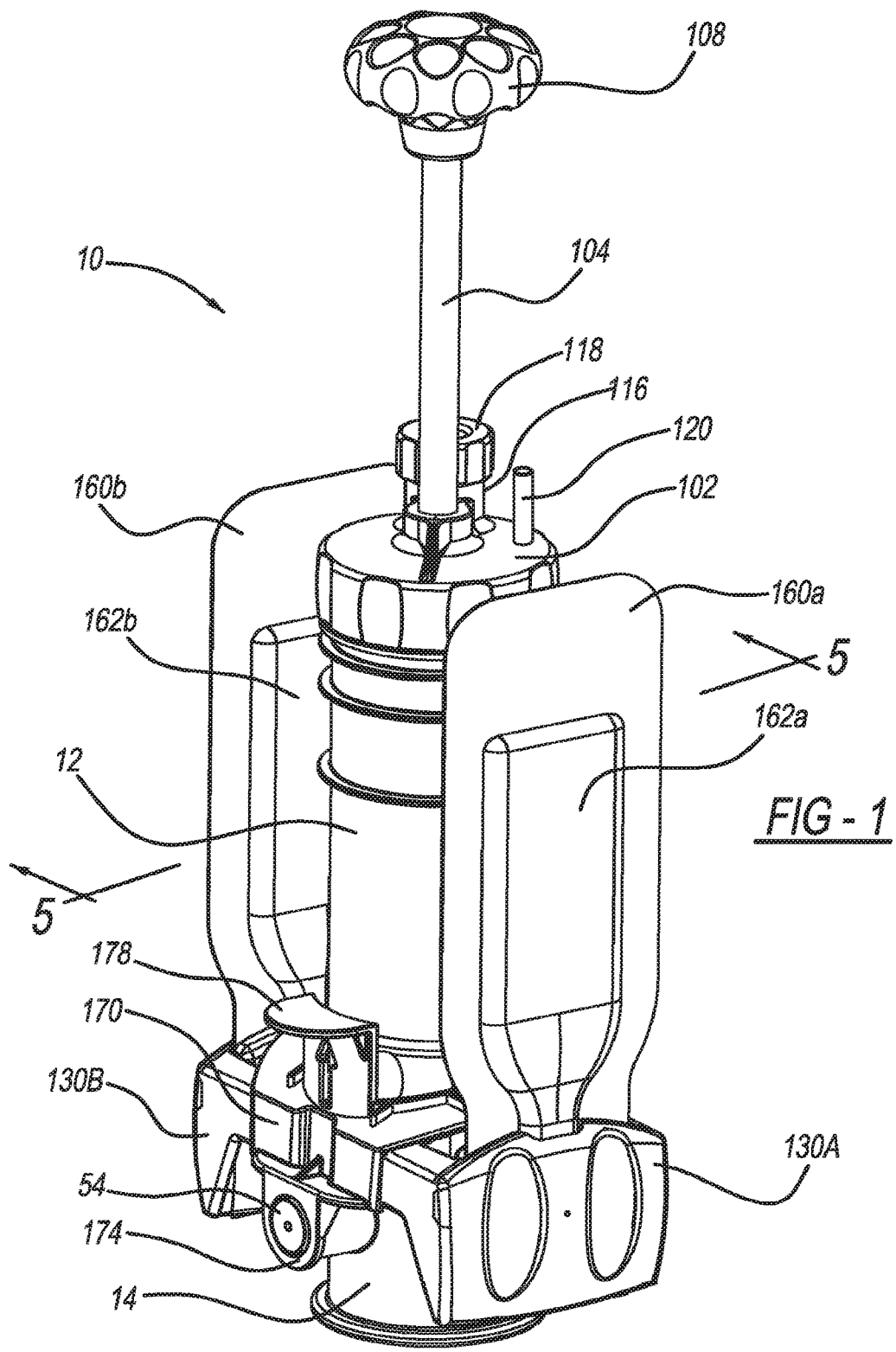
FIG. 1 is a perspective view of a device for storing and mixing bone cement components according to the present teachings.
Figure 2:
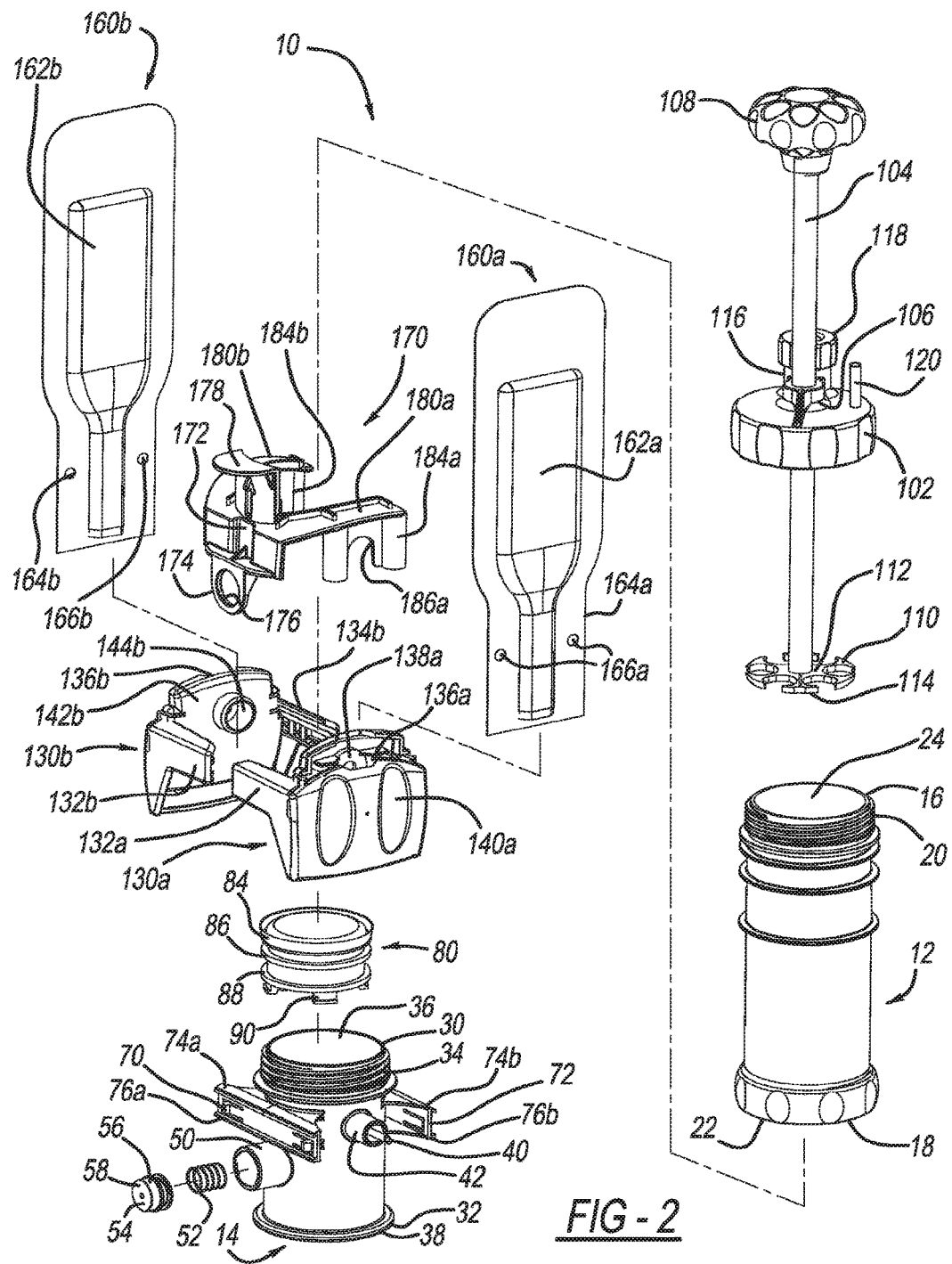
FIG. 2 is a exploded view of the device of FIG. 1.

With initial reference to FIGS. 1 and 2, a device for storing and mixing bone cement components, such as liquid and powder components, is generally illustrated at reference numeral 10. The device 10 can be used with any suitable bone cement. The powder component can be of a variety of different materials in a variety of different forms. For example, the powder can be a poly (methyl methacrylate) or methyl methacrylate-styrene homo- or copolymer. The powder component can also include various other forms or morphologies, such as spherical beads that can be obtained by any conventional suspension polymerization process. The beads can be sieved to comply with particular size specifications. The powder component can also include particles that have been milled or crushed, such as benzoyle peroxide at about 1% to about 5% and radiopacifiers, such as barium sulfate and zircronum dioxide. Furthermore, the powder component can include particles of antibiotics, such as Gentamicyn, Clindamicyn. The liquid component can be a variety of different materials in a variety of different forms. For example, the liquid component can be a methyl methacrylate monomer liquid. In addition, a polymerization accelerator, such as about 0.5% to about 4% dimethyl-para-toluidine, and/or a stabilizer in monomer hydro-quinone at 10-100 ppm can be used.

Figure 5:
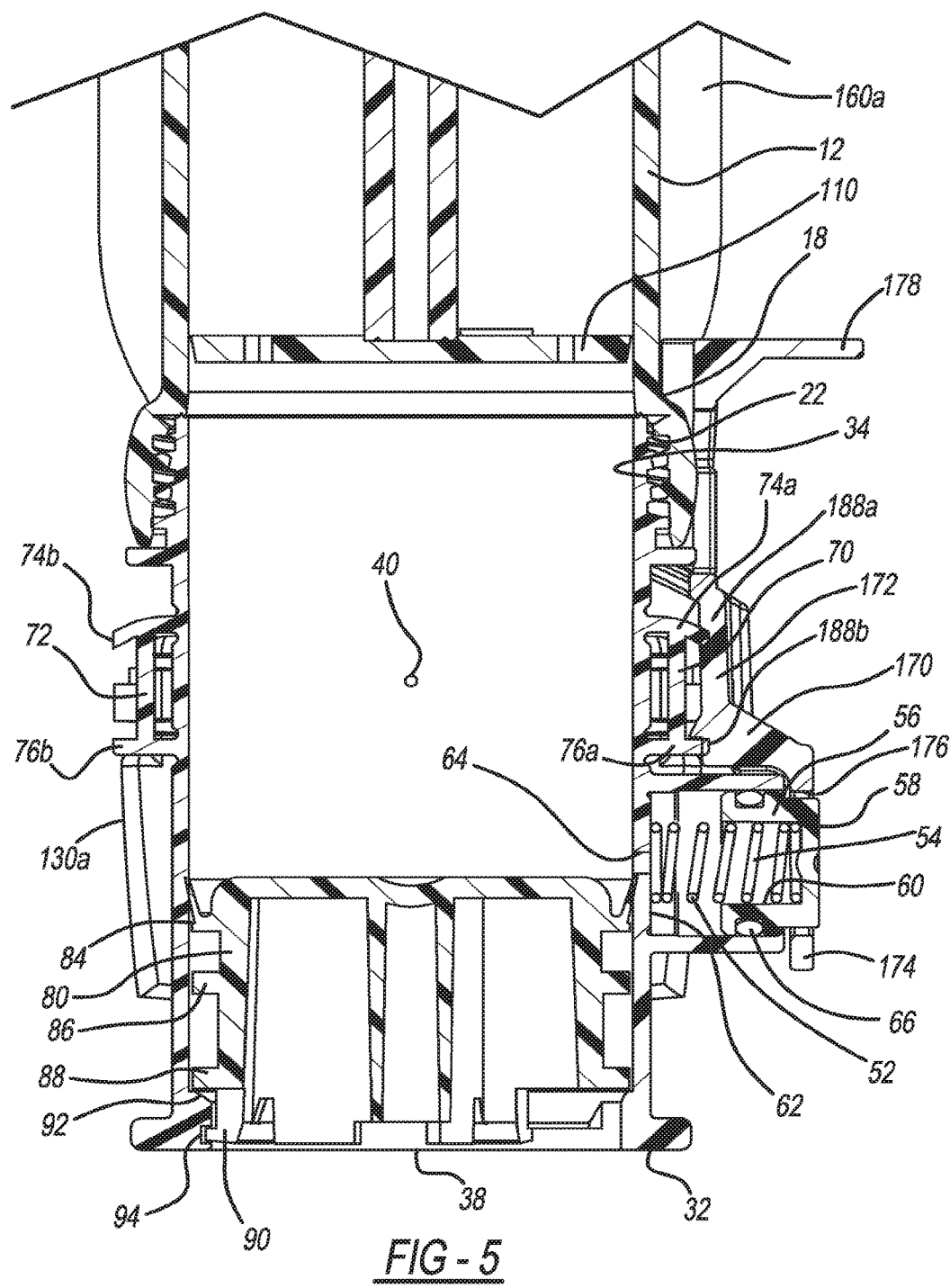
FIG. 5 is a cross-sectional view of the device of FIG. 1 taken along line 5-5 of FIG. 1.

The device 10 includes a housing having a first housing portion 12 and a second housing portion 14. With reference to FIG. 2 for example, the first housing portion 12 includes a proximal end 16 and a distal end 18, which is opposite to the proximal end 16. At the proximal end 16 is a proximal coupling member 20. The proximal coupling member 20 can be any suitable coupling member, such as external threads as illustrated. A distal end coupling member 22 is at the distal end 18. The distal end coupling member 22 can be any suitable coupling member, such as an internally threaded coupling member, as illustrated in FIG. 5 for example. The first housing portion 12 defines a first mixing chamber portion 24 of the device 10.

The second housing portion 14 includes a proximal end 30 and a distal end 32, which is opposite to the proximal end 30. At the proximal end 30 is a proximal coupling member 34. The proximal coupling member 34 can be any suitable coupling member, such as external threads as illustrated. The second housing portion 14 defines a second mixing chamber portion 36 of the device 10. The first and second mixing chamber portions 24 and 36 together define a mixing chamber of the device 10, which can include the powder component of bone cement. An outlet 38 of the second mixing chamber portion 36 is at the distal end 32 of the second housing portion 14. The second housing portion 14 is coupled to the first housing portion 12 through cooperation between the distal end coupling member 22 of the first housing portion 12 and the proximal coupling member 34 of the second housing portion 14, as illustrated in FIG. 5, for example.

Figure 9:
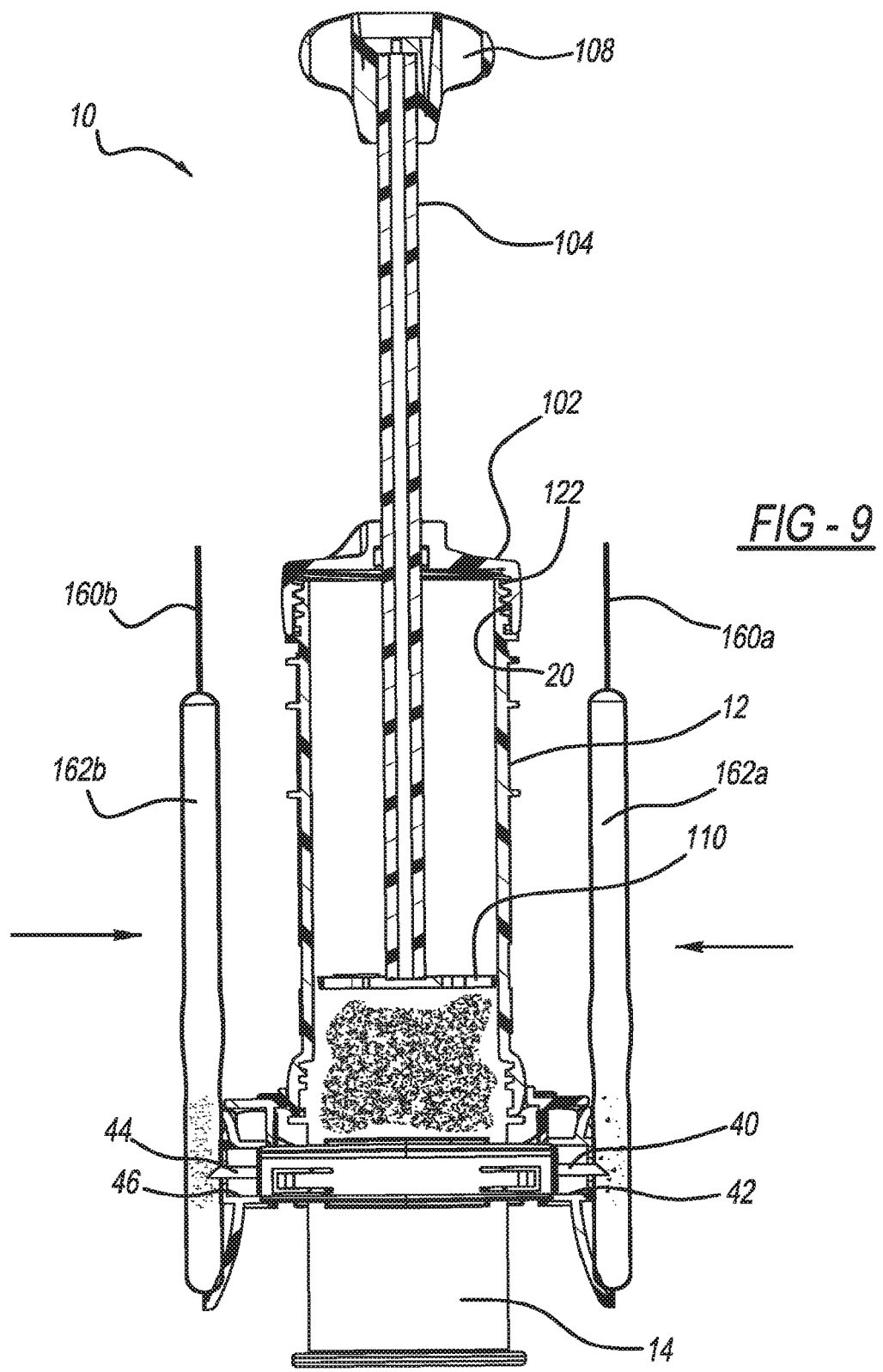
FIG. 9 is a cross-sectional view of the device of FIG. 1 with the first and second container supports illustrated in the second position.

The second housing portion 14 includes a first radially extending piercing cannula 40 extending therefrom. The first piercing cannula 40 is in cooperation with the second mixing chamber portion 36. The first piercing cannula 40 includes a pointed distal tip configured to pierce and penetrate a container including a liquid bone cement component as described herein to permit the liquid bone cement to be extracted therefrom as described herein. The first piercing cannula 40 is surrounded by a first cannula housing 42 extending from the second housing portion 14. As illustrated in FIG. 9 for example, a second piercing cannula 44 extends from the second housing portion 14 in a direction opposite to the first piercing cannula 40. The second piercing cannula 44 is surrounded by a second cannula housing 46. The second piercing cannula 44 is similar to the first piercing cannula 40, and the second cannula housing 46 is similar to the first cannula housing 42. The first piercing cannula 40 and the second piercing cannula 44 are generally on opposite sides of the second housing portion 14 and extend perpendicular to a longitudinal axis of the housing 42. The second piercing cannula 44 is optional and need not be included.

Figure 7:
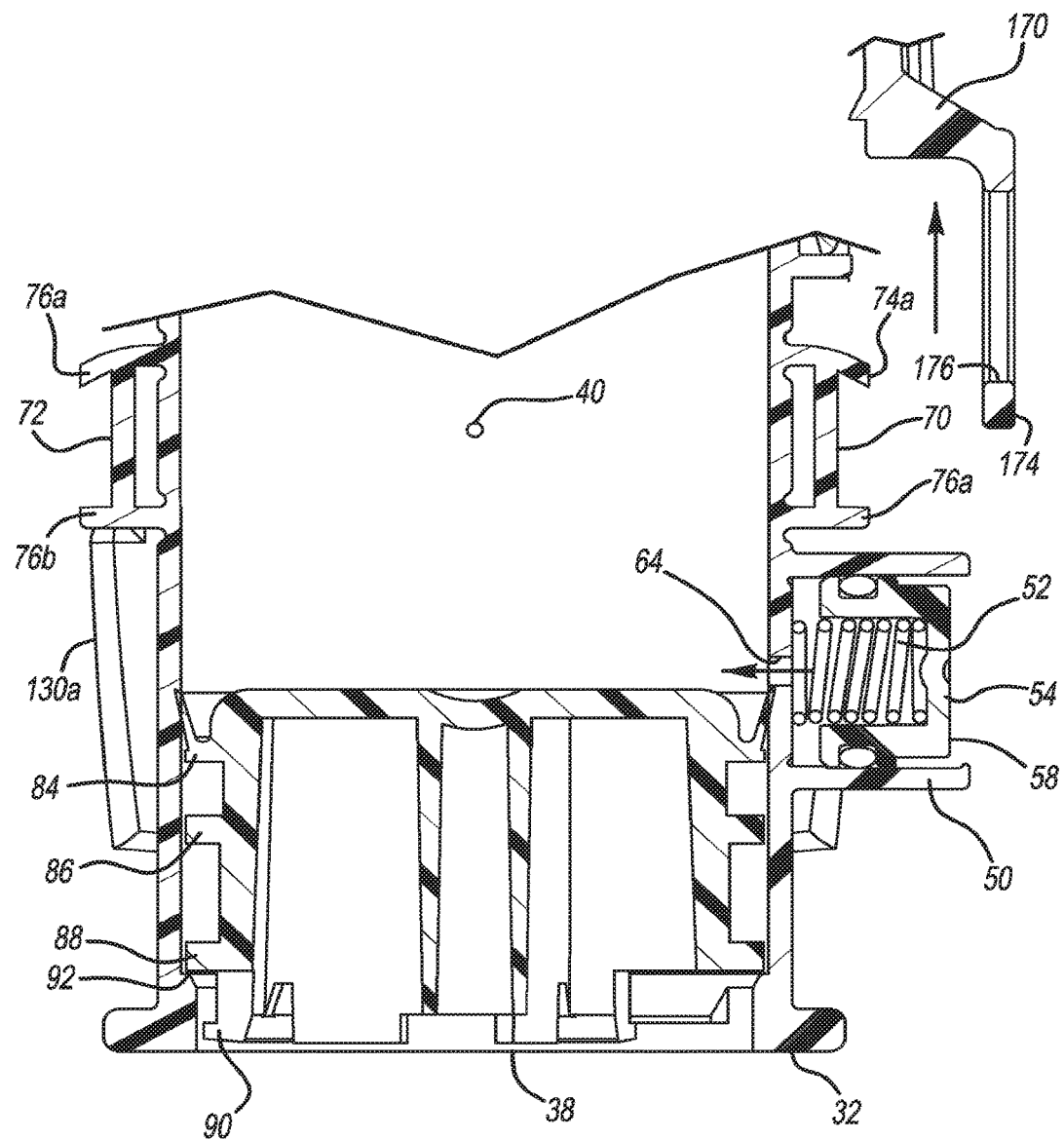
FIG. 7 is a cross-sectional view taken along line 7-7 of FIG. 6 of a vacuum indicator of the device having been moved from a first position (FIG. 5) to a second position as illustrated.

An indicator housing 50 extends radially from the second housing portion 14. Seated within the indicator housing 50 is a spring 52 and a vacuum indicator, which can be a piston 54 for example, as illustrated. As illustrated in FIG. 2 and FIG. 5, the piston 54 includes a body 56 with an outer surface 58. The body 56 defines an inner cavity 60, which the spring 52 is seated within (see FIG. 5). The spring 52 also abuts an outer surface 62 of the second housing portion 14 surrounded by the indicator housing 50. The indicator housing 50 is in communication with the second mixing chamber portion 36 by way of a passageway 64 defined by the outer surface 62 and extending to the second mixing chamber portion 36. A washer or any suitable seal 66 surrounds the body 56. The spring 52 biases the piston 54 in the outward or first configuration of FIG. 5. As further described herein, the piston 54 is movable to a second or retracted position in response to pressure of the first and second mixing chamber portions 24 and 36 being reduced below a predetermined threshold, as illustrated in FIG. 7 for example. In the first configuration of FIG. 5, the outer surface 58 of the piston 54 extends out from within the indicator housing 50. In the second position of FIG. 7, the outer surface 58 is recessed within the indicator housing.

The second housing portion 14 further includes a first retention member 70 and a second retention member 72. The first and second retention members 70 and 72 are generally on opposite sides of the second housing portion 14. The first and second piercing cannulas 40 and 44 are between the first and second retention members 70 and 72. The first retention member 70 includes a proximal rail 74a and a distal rail 76a. The proximal and distal rails 74a and 76a extend generally spaced apart and parallel to one another. The second retention member 72 is substantially similar to the first retention member 70, and thus includes a proximal rail 74b and a distal rail 76b. The proximal rail 74b and the distal rail 76b extend generally parallel to one another and are spaced apart.

An insert for the second housing portion 14 is illustrated at reference numeral 80. Extending from an outer periphery of the insert 80 is a proximal rim 84, an intermediate rim 86, and a distal rim 88. A plurality of spaced apart locking flanges 90 extend from the insert 80 proximate to the distal rim 88. As illustrated in FIG. 5, the insert 80 is seated within the second housing portion 14 at the distal end 32 thereof such that the distal rim 88 is seated on an inner distal flange 92 defined at an interior of the second housing portion 14 to support the insert 80 therein. The locking flanges 90 couple with corresponding recesses 94 of the second housing portion 14 to secure the insert 80 at the distal end 32 of the second housing portion 14.

The device 10 further includes a cap 102 and a plunger rod 104 extending through a plunger aperture 106 defined by the cap 102. At a first end of the plunger rod 104 is a handle 108, and at a second end of the plunger rod 104 opposite to the handle 108 is a mixer 110. The mixer 110 includes a center portion 112 to which the plunger rod 104 is mounted. Extending from the plunger rod 104 is a plurality of spaced apart mixing fins 114. The cap 102 defines a first port 116, which is illustrated as covered by cap 118, and a second port 120. Contents of the first and second housing portions 12 and 14 can be extracted through the first port 116 after removal of the cap 118. The second port 120 can be connected to a vacuum source, such as the vacuum source 210 described herein, with any suitable connector, such as connection tube 212. At an interior of the cap 102 are threads 122 (FIG. 9, for example), which are configured to couple with the proximal coupling member 20 of the first housing portion 12 to secure the cap 102 to the first housing portion 12. The threads 122 can be any suitable coupling member to connect the cap 102 to the first housing portion 12.

Figure 3:
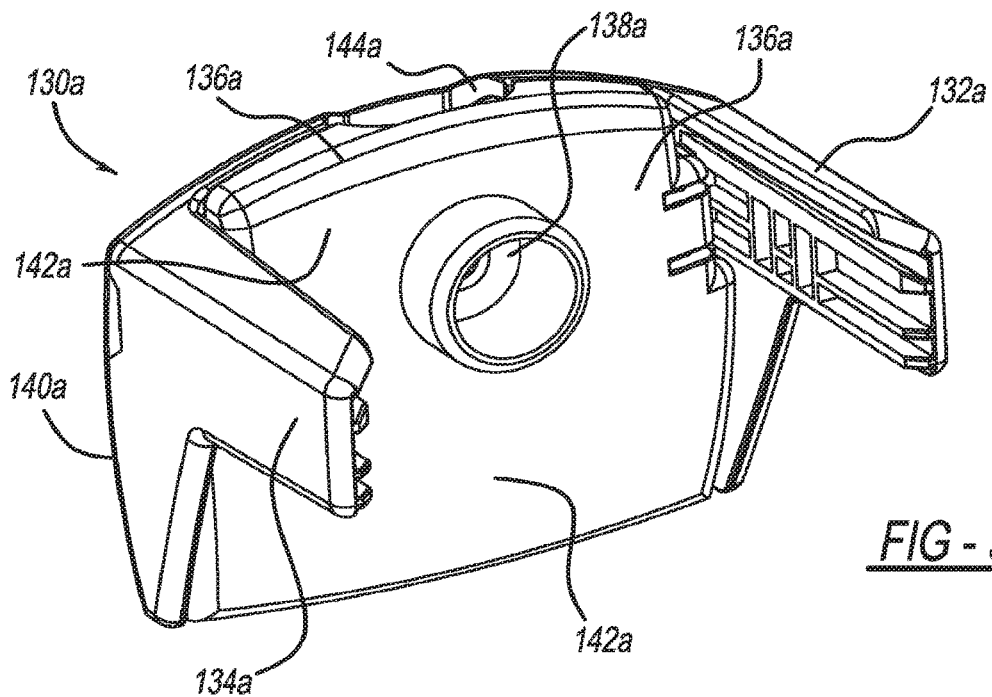
FIG. 3 is a perspective view of a container support of the device of FIG. 1.
Figure 4:
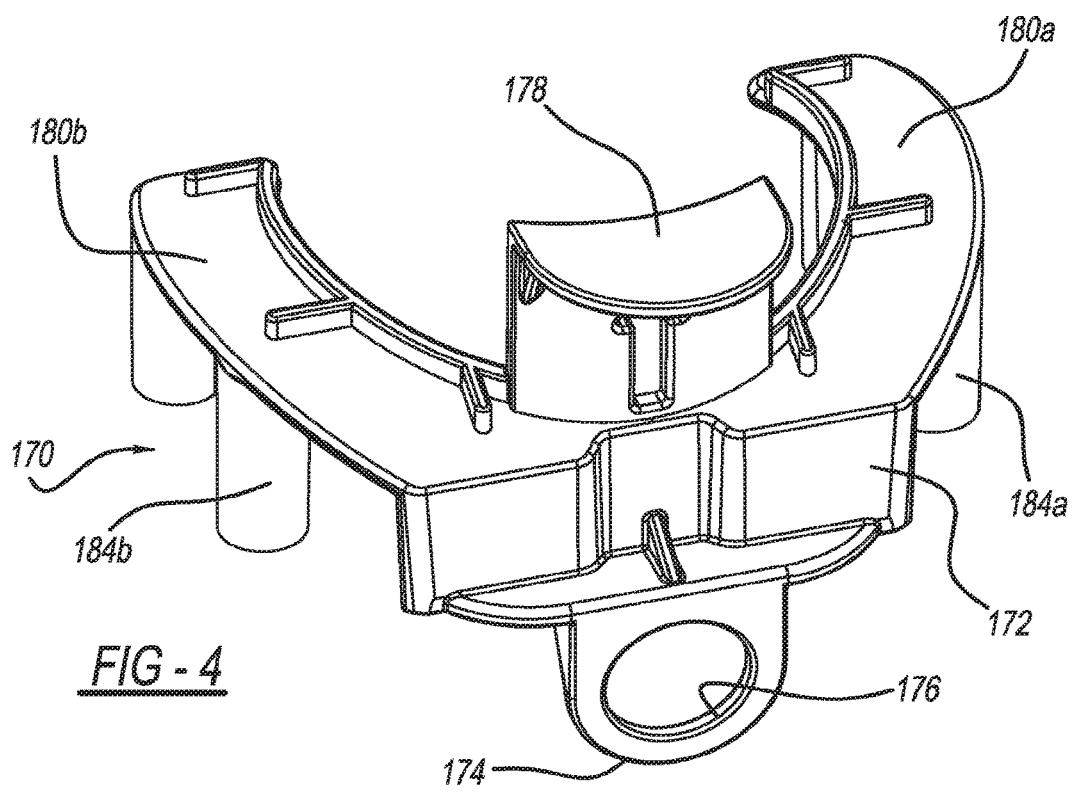
FIG. 4 is a perspective view of a safety insert of the device of FIG. 1.

Coupled to the first and second retention members 70 and 72 is a first container support 130a and a second container support 130b. The second container support 130b is optional and need not be included. With continued reference to FIG. 2 and additional reference to FIG. 3, the first container support 130a includes a first flange 132a and a second flange 134a. The first container support 130a defines a first slot 136a and a first cannula receptacle 138a configured to receive the first piercing cannula 40 therein. A first outer surface 140a of the first container support 130a is opposite to a first inner surface 142a. The first slot 136a is between the first outer surface 140a and the first inner surface 142a. Extending from the first inner surface 142a is a first cannula boss 144a, which surrounds the first cannula receptacle 138a. The first cannula receptacle 138a extends through the first inner surface 142a to provide a passageway to the first slot 136a. The first cannula boss 144a is sized and shaped to receive the first cannula housing 42 therein. The second container support 130b is substantially similar to the first container support 130a. Therefore, the description of the first container support 130a also applies to the second container support 130b. Features in common between the first and second container supports 130a and 130b are referenced in the figures with respect to second container support 130b using the same reference numbers, but with the letter "b" instead of the letter "a."

With respect to the first container support 130a, the first flange 132a is slidably coupled to the first retention member 70 and the second flange 134a is slidably coupled to the second retention member 72. With respect to the second container support 130b, the first flange 132b is slidably coupled to the first retention member 70 and the second flange 134b is slidably coupled to the second retention member 72.

A first container 160a is seated within the first slot 136a of the first container support 130a. The first container 160a defines a receptacle 162a configured to store a liquid component of bone cement therein. The first container 160a defines a tapered portion 164a and retention members 166a. A tapered portion 164a is seated within the first slot 136a, and secured therein through cooperation between retention members 166a and corresponding retention members within the first slot 136a. The first container 160a can be any suitable container for storing the liquid component of bone cement therein, such as a flexible polymeric container.

A second container 160b is substantially similar to the first container 160a. The second container 160b is optional and need not be included, such as when the second container support 130b is not included. Features of the second container 160b are identified in the drawings with in the same reference numbers used to identify features in common with the first container 160a, but include the letter "b" instead of the letter "a." The second container 160b is seated within the second slot 136b defined by the second container support 130b.

A safety insert for the device 10 is illustrated at reference number 170. The safety insert 170 includes a main body 172 and a flange 174 extending therefrom. The flange 174 defines an aperture 176, which is sized and shaped to receive the piston 54 therein. A tab 178 extends from an end of the main body 172 opposite to the flange 174. The tab 178 can be configured in any suitable manner to facilitate removal of the safety insert 170 from cooperation with the first and second housing portions 12 and 14 as described herein. Extending from opposite ends of the main body 172 are a first arm 180a and a second arm 180b. The first and second arms 180a and 180b extend from the same side of the main body 172. The first arm 180a includes a first stop 184a, which extends from the first arm 180a in the same direction that the flange 174 does, and defines an aperture 186a. The second arm 180b includes a similar second stop 184b and aperture 186b.

Figure 6:
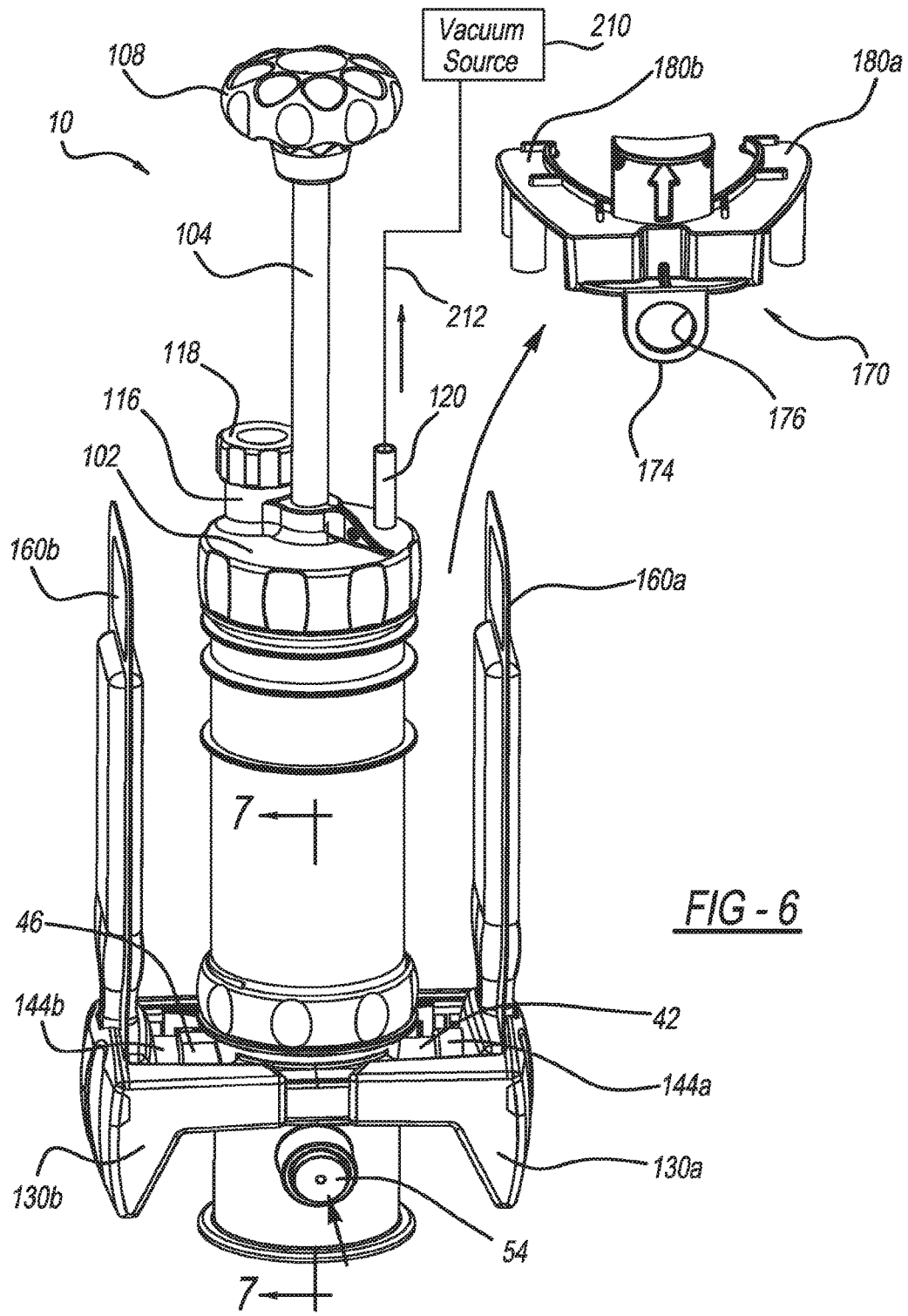
FIG. 6 illustrates the device of FIG. 1 coupled to a vacuum source to provide the device with a reduced internal pressure and a safety insert removed from cooperation with the device.

An exemplary operation of the device 10 will now be described. With reference to FIG. 6, upon activation of vacuum source 210 with line 212 connected to the second port 120, air will be drawn from within the first and second mixing chamber portions 24 and 36 to lower the air pressure therein. The pressure within the first and second mixing chamber portions 24 and 36 can be lowered to any suitable level, such as 0.78 Bar for example, which can be a predetermined threshold pressure. Upon reaching this threshold pressure, or any other suitable predetermined pressure, the vacuum indicator or piston 54 moves from the first position of FIG. 5 to the second position of FIGS. 6 and 7. More specifically, reduction of air pressure within the second mixing chamber portion 36 draws air out from within the indicator housing 50 through the passageway 64 and into the second mixing chamber portion 36. As air is drawn out from the within the indicator housing 50, the piston 54 is drawn radially inward towards the outer surface 62 in the passageway 64 in a direction generally perpendicular to the longitudinal axis of the housing 50.

In the first position, the piston 54 is arranged such that a portion of the body 56 adjacent to the outer surface 58 extends through the aperture 176 defined by the flange 174 of the safety insert 170, as illustrated in FIG. 5. With the piston 54 arranged in this first position, the safety insert 170 cannot be removed from cooperation with the first and second housing portions 12 and 14, as illustrated in FIGS. 1 and 5 for example. The safety insert 170 is further coupled to the second housing portion 14 through cooperation with the proximal rail 74a and the distal rail 76a of the first retention member 70, as illustrated in FIG. 5 for example. More specifically, the proximal rail 74a is seated within a proximal recess 188a of the main body 172 at the safety insert 170, and the distal rail 76a is seated within distal recess 188b of the main body 172.

With the safety insert 170 coupled to the second housing portion 14 as illustrated in FIG. 1, for example, the first and second container supports 130a and 130b are retained in the expanded or deactivated position of FIG. 1. More specifically, the first arm 180a of the safety insert 170 is positioned between the first container support 130a and the second housing portion 14 with the first stop 184a arranged such that the first cannula housing 42 is seated within the aperture 186a. Similarly, the second arm 180b is arranged between the second container support 130b and the second housing portion 14 such that the second cannula housing 46 is seated within the second aperture 186b.

Figure 8:
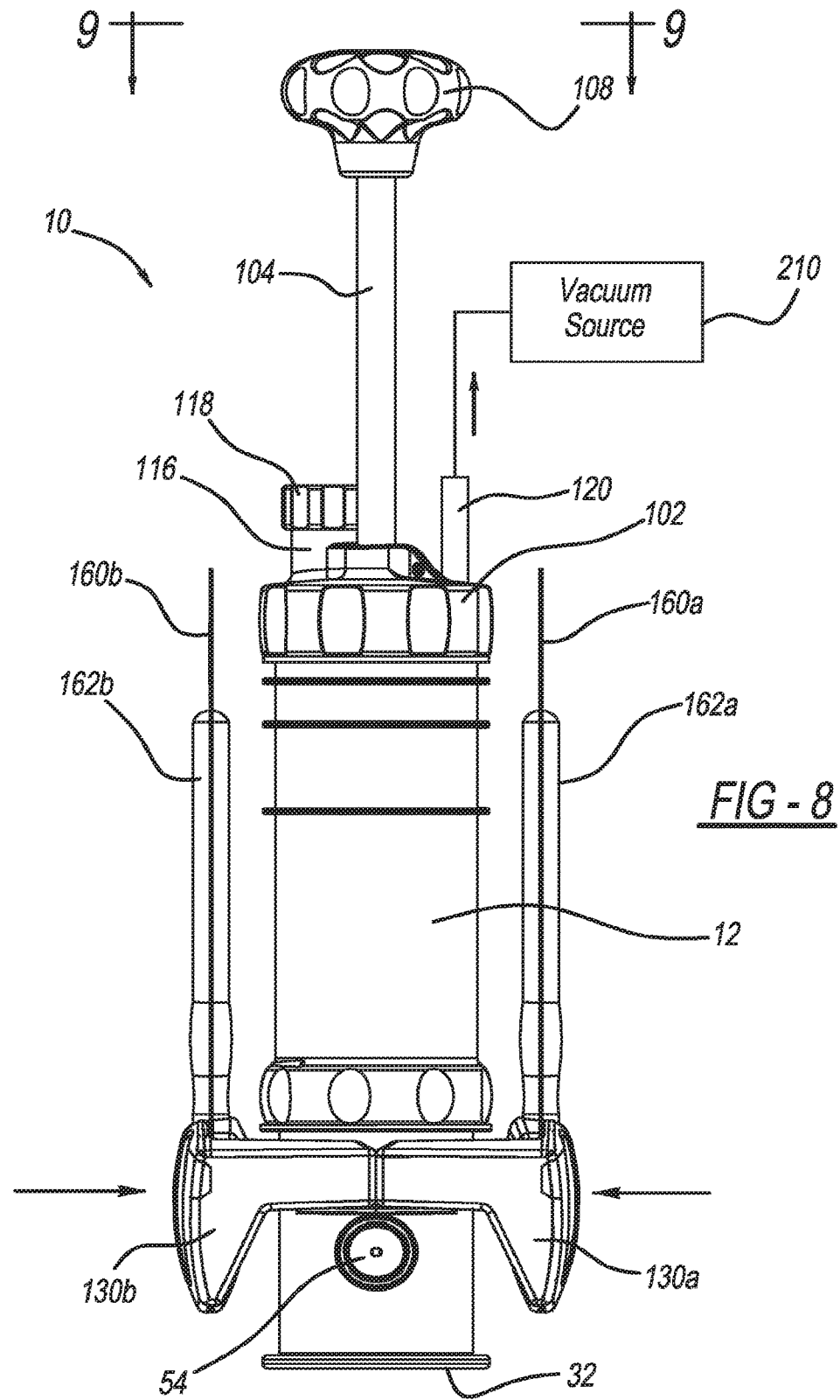
FIG. 8 is a side view of the device of FIG. 1, with first and second supports having been moved from a first position (FIG. 6) to a second position as illustrated.

With reference to FIGS. 6 and 7, when the piston 54 moves to the second position of FIGS. 6 and 7 in response to the predetermined pressure being reached within the first and second mixing chamber portions 24 and 36, the body 56 will not extend through the aperture 176 of the safety insert 170, thereby permitting removal of the safety insert 170 from cooperation with the second housing portion 14. With the safety insert 170 removed, it no longer impedes movement of the first and second container supports 130a and 130b together along the first and second retention members 70 and 72. Therefore, the first and second container supports 130a and 130b can be moved together to a retracted or activated position, as illustrated in FIG. 8. The first piercing cannula 40 pierces and penetrates the liquid component receptacle 162a as the first container 160a is pushed onto the first piercing cannula 40 in response to movement of the first container support 130a to the active position of FIGS. 8 and 9. Similarly, the second piercing cannula 44 pierces and penetrates the liquid component receptacle 162b of the second container 160b when the second container support 130b is moved to the activated position of FIGS. 8 and 9.

Due to the decreased pressure within the first and second mixing chambers 24 and 36, the liquid component of bone cement stored within the liquid component receptacles 162a and 162b is drawn out from within the liquid component receptacles 162a and 162b through the first and second piercing cannulas 40 and 44 respectively and into the second mixing chamber portion 36, where the liquid component of bone cement mixes with the powder component of bone cement stored therein. To further mix and prepare the bone cement, the mixer 110 can be rotated and/or moved longitudinally through the first and second mixing chamber portions 24 and 36 using the handle 108 coupled to the plunger rod 104. After the liquid and powder bone cement components have been sufficiently mixed, they can be extracted out from within the first and second mixing chamber portions 24 and 36 through the first port 116 for delivery to a desired area.

The present teachings therefore provide a device and method to ensure that surgical staff mixes the bone cement under the proper vacuum, which ensures that the mixed bone cement does not include excessive amounts of air therein. For example, if the air pressure within the first and second mixing chamber portions 24 and 36 is not at or lower than the predetermined threshold, the piston 54 will not move to the second position, and thus will prevent removal of the safety insert 170 from cooperation with the second housing portion 14 in which the first and second arms 180a and 180b prevent movement of the first and second container supports 130a and 130b together to the activated position of FIGS. 8 and 9. During use of the device 10, if the pressure within the first and second mixing chamber portions 24 and 36 rises back above the predetermined threshold, the spring 52 of the piston 54 will force the piston back outward to the first position, which will give the operator a visual indicator that the pressure is no longer at or below the predetermined threshold.

Figure 10:
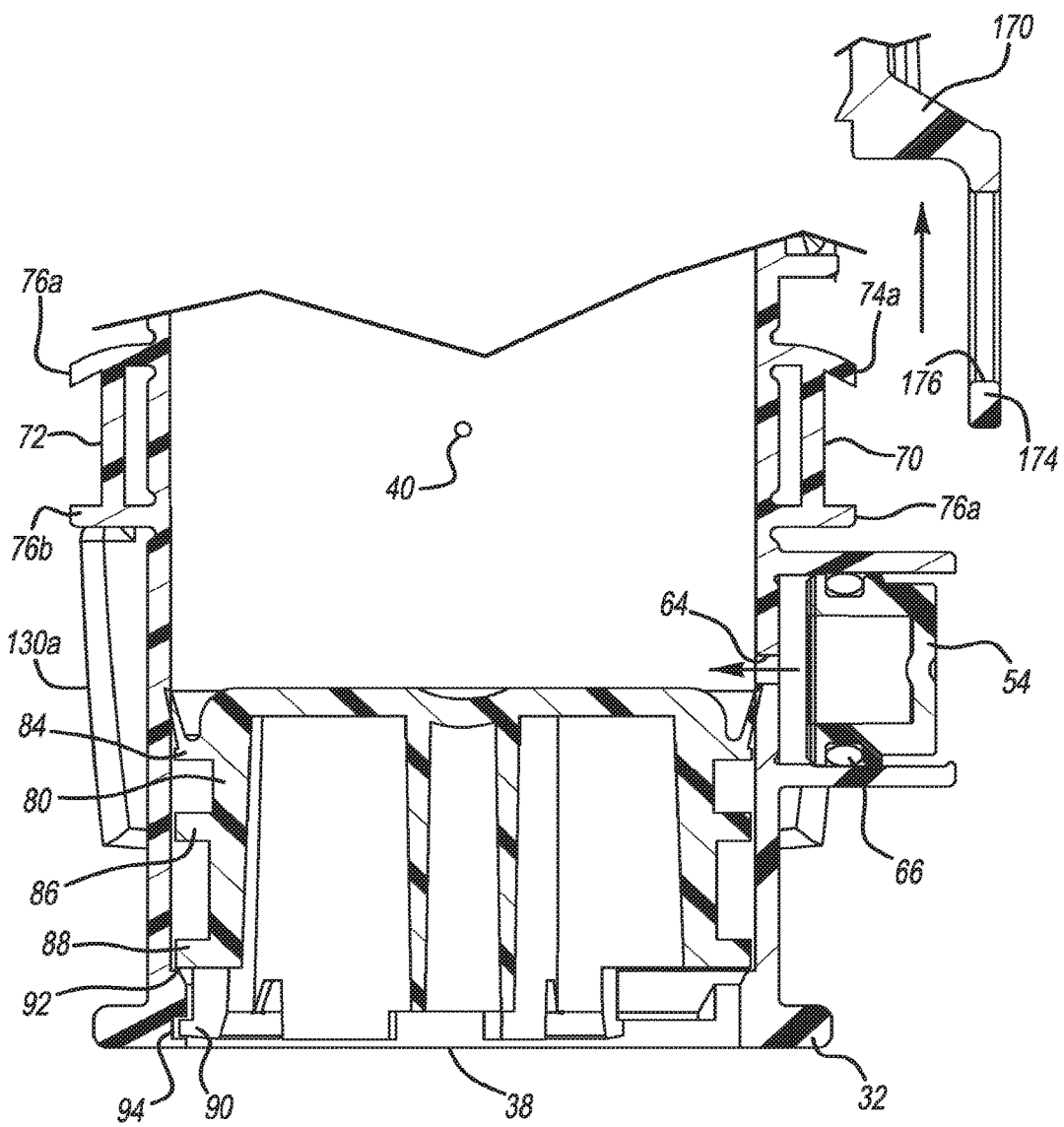
FIG. 10 is a cross-sectional view of the device of FIG. 1 including an additional vacuum indicator according to the present teachings, the view is taken along a line similar to line 5-5 of FIG. 1.

With reference to FIG. 10, the piston 54 need not include the spring 52, and thus the piston 54 can be retained in the first position by a friction fit with an interior of the indicator housing 50. The washer or seal 66 can enhance the friction fit with the indicator housing 50.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method, comprising:
    creating a vacuum within a mixing chamber in a housing containing a first bone cement component to decrease pressure therein below a threshold level thereby causing a vacuum indicator to move from a first indicator position, wherein the vacuum indicator couples with a safety device to restrict movement of the safety device from a safety position to avoid contact between the first bone cement component and a second bone cement component in the mixing chamber, to a second indicator position, wherein the vacuum indicator permits movement of the safety device out of the safety position to allow contact between the first bone cement component and the second bone cement component in the mixing chamber;
    moving the safety device out of the safety position; and
    mixing the first bone cement component and the second bone cement component together in the mixing chamber to form a bone cement mixture.

2. The method of claim 1, wherein the safety device does not impede moving a first container towards the housing when the safety device is out of the safety position, the first container containing at least a portion of the second bone cement component and being movably mounted to the housing via a first container support; and
    further comprising moving the first container along the first container support such that a first piercing cannula penetrates the first container, wherein the first piercing cannula is in communication with the mixing chamber such that the second bone cement component within the first container is drawn into the mixing chamber due to the reduced pressure therein.

3. The method of claim 2, wherein the safety device does not impede moving a second container towards the housing when the safety device is out of the safety position, the second container containing a portion of the second bone cement component and being movably mounted to the housing via a second container support; and further comprising moving the second container along the second container support such that a second piercing cannula penetrates the second container, wherein the second piercing cannula is in communication with the mixing chamber such that the second bone cement component within the second container is drawn into the mixing chamber due to the reduced pressure therein.

4. The method of claim 1, further comprising coupling a vacuum line to the mixing chamber to create the vacuum therein, the vacuum line connected to a vacuum source.

5. The method of claim 4, further comprising activating the vacuum source.

6. The method of claim 5, further comprising monitoring a vacuum level within the mixing chamber by monitoring the position of the vacuum indicator, which moves corresponding to both increases and decreases in the vacuum level.

7. The method of claim 1, further comprising dispensing the bone cement mixture from within the mixing chamber.

8. The method of claim 7, further comprising causing the vacuum indicator to move back to the first indicator position if the pressure in the mixing chamber exceeds the threshold level.

9. The method of claim 1,
wherein creating a vacuum within a mixing chamber to decrease pressure therein below a threshold level further comprises decreasing the pressure to at least 0.78 Bar.

10. The method of claim 1, further comprising rotating a mixer in the mixing chamber to further mix the first bone cement component and the second bone cement component.

11. The method of claim 1, further comprising moving a mixer in the mixing chamber along a longitudinal mixing chamber axis to further mix the first bone cement component and the second bone cement component.

12. A method, comprising:
creating a vacuum within a mixing chamber in a housing containing a first bone cement component to decrease pressure therein below a threshold level thereby causing a vacuum indicator to move from a first indicator position, wherein the vacuum indicator couples with a safety device to restrict movement of the safety device from a safety position to avoid contact between the first bone cement component and a second bone cement component in the mixing chamber, to a second indicator position, wherein the vacuum indicator permits movement of the safety device out of the safety position to allow contact between the first bone cement component and the second bone cement component in the mixing chamber;
moving the safety device out of the safety position; and
mixing the first bone cement component and the second bone cement component together in the mixing chamber to form a bone cement mixture including actuating a mixer in the mixing chamber to further mix the first bone cement component and the second bone cement component.

13. The method of claim 12, wherein the safety device does not impede moving a first container towards the housing when the safety device is out of the safety position, the first container containing at least a portion of the second bone cement component and being movably mounted to the housing via a first container support; and
further comprising moving the first container along the first container support such that a first piercing cannula penetrates the first container, wherein the first piercing cannula is in communication with the mixing chamber such that the second bone cement component within the first container is drawn into the mixing chamber due to the reduced pressure therein.

14. The method of claim 13, wherein the safety device does not impede moving a second container towards the housing when the safety device is out of the safety position, the second container containing a portion of the second bone cement component and being movably mounted to the housing via a second container support; and
further comprising moving the second container along the second container support such that a second piercing cannula penetrates the second container, wherein the second piercing cannula is in communication with the mixing chamber such that the second bone cement component within the second container is drawn into the mixing chamber due to the reduced pressure therein.

15. The method of claim 12, further comprising coupling a vacuum line to the mixing chamber to create the vacuum therein, the vacuum line connected to a vacuum source.

16. The method of claim 15, further comprising activating the vacuum source.

17. The method of claim 16, further comprising monitoring a vacuum level within the mixing chamber by monitoring the position of the vacuum indicator, which moves corresponding to both increases and decreases in the vacuum level.

18. The method of claim 12, further comprising dispensing the bone cement mixture from within the mixing chamber.

19. The method of claim 18, further comprising causing the vacuum indicator to move back to the first indicator position if the pressure in the mixing chamber exceeds the threshold value.

20. The method of claim 12, wherein creating a vacuum within a mixing chamber to decrease pressure therein below a threshold level further comprises decreasing the pressure to at least 0.78 Bar.

* * * * *